United States Patent [19]
Knoch et al.

[11] Patent Number: 5,309,900
[45] Date of Patent: May 10, 1994

[54] ATOMIZER PARTICULARLY FOR USE IN DEVICES FOR INHALATION THERAPY

[75] Inventors: Martin Knoch, Berg; Stephan Brugger, Starnberg, both of Fed. Rep. of Germany

[73] Assignee: Paul Ritzau Pari-Werk GmbH, Fed. Rep. of Germany

[21] Appl. No.: 774,080

[22] Filed: Oct. 9, 1991

[30] Foreign Application Priority Data

Mar. 21, 1991 [EP] European Pat. Off. ......... 91104439.4

[51] Int. Cl.$^5$ ............................................. A61M 11/00
[52] U.S. Cl. ........................... 128/200.14; 128/200.24; 128/203.12
[58] Field of Search ....................... 128/200.21, 200.11, 128/200.18, 203.12, 200.14, 200.24, 203.16, 204.14, 911, 912; 239/338, 370; 261/DIG. 65, DIG. 83

[56] References Cited

U.S. PATENT DOCUMENTS

| | | | |
|---|---|---|---|
| D. 263,337 | 3/1982 | Hart | D24/62 |
| 3,362,405 | 1/1968 | Hazel | 128/203.15 |
| 3,962,381 | 6/1976 | Farrish | 261/141 |
| 4,086,305 | 4/1978 | Dobritz | 261/30 |
| 4,429,835 | 2/1984 | Brugger | 239/338 |
| 4,430,994 | 2/1984 | Clawson | 128/203.27 |
| 4,951,661 | 8/1990 | Sladek | 128/202.27 |
| 4,993,411 | 2/1991 | Callaway | 128/204.14 |

FOREIGN PATENT DOCUMENTS

| | | | |
|---|---|---|---|
| 603505 | 8/1960 | Canada | 128/204.13 |
| 111003 | 8/1964 | Czechoslovakia | 128/200.11 |
| 052284 | 5/1982 | European Pat. Off. | |
| 237507 | 9/1987 | European Pat. Off. | |
| 157216 | 10/1939 | Fed. Rep. of Germany | 128/203.12 |
| 849172 | 9/1952 | Fed. Rep. of Germany | 128/200.18 |
| 777286 | 2/1935 | France | 128/200.21 |
| 2638362 | 11/1989 | France | |
| 9015635 | 12/1990 | World Int. Prop. O. | 128/203.15 |

*Primary Examiner*—Edgar S. Burr
*Assistant Examiner*—Eric P. Raciti
*Attorney, Agent, or Firm*—Brooks, Haidt, Haffner & Delahunty

[57] ABSTRACT

Inhalation therapy is not only used for the treatment of respiratory tract diseases, but also increasingly for administering other medicinal substances. In this kind of therapy, the substance is made available to the patient for inhalation in the form of a liquid vapor having very small droplet diameters (ca. 1 to 5 um) and is transported together with the inhaled air into the respiratory tracts. The inventive atomizer consists of a cylindrical atomizing space with two openings for respectively supplying and withdrawing the liquid vapor, the openings being arranged in such a manner that a spiral vortex is formed which extends about the longitidunal axis of the atomizing space.

14 Claims, 2 Drawing Sheets

ATOMIZER PARTICULARLY FOR USE IN DEVICES FOR INHALATION THERAPY

BACKGROUND OF THE INVENTION

1. Field of the Invention

The invention relates to an atomizer particularly for use in devices for inhalation therapy.

2. Related Art

Inhalation therapy is not only used for treating respiratory tract diseases but also, to an increasing extent, for administering other medicinal active substances. In this kind of therapy, the substance is offered to the patient for inhalation in the form of a vaporized liquid with a very small droplet diameter (less than 5 um) and is transported together with the breath into the respiratory tracts. For the reliable intake of this active substance, it is required that the vaporized liquid, and the active substance carried with it, is transported by the flow of breath far into the respiratory tracts without it depositing prematurely in the mouth and throat area. Only the transport into the deep respiratory tracts ensures an effective absorption of the active substance via the surface of the lungs. Furthermore, a synchronous coordination between the inhalation act and the generation, or making available, of the vaporized liquid is always required with the aim of providing a sufficient and simultaneously ascertainable quantity of the vaporized liquid for the dosage during the breathing act. In view of both of these requirements, it has been already recognized, in the use of dosing-aerosols, that a stream of vaporized liquid generated by means of spray diffuser, introduced into the inhaled air stream by the breathing act, is introduced in too strong a bundled manner into the mouth and throat area so that the desired transport into the deep respiratory tracts is not achieved. Stilling chambers, in the form, for example, of an extended mouthpiece between the atomizing location and the inhalation location, were therefore suggested which should lead to a distribution and deceleration of the vaporized liquid and enable an uncoordinated inhalation after the resulting atomization. In these, in the broadest sense cylindrically shaped stilling chambers, the liquid vapor enters into the hollow space of the stilling chamber at one front end and, due to the cross-sectional enlargement at the transition from the feed connection to the inside of the stilling chamber, an uncontrolled turbulance and, as a whole, a deceleration of the liquid droplets occurs in the stream flow. The vaporized liquid is drawn off in the breathing-in phase of the inhalation act at the opposing front end of the stilling chamber. However, as a rule in such systems, a single draw of breath does not suffice to draw the entire aerosol volume out of the stilling chamber.

In order that a sufficient quantity of the vaporized liquid is provided for the inhalation step, the hollow space of the stilling chamber must be relatively large so that dead spaces can arise in which the vaporized liquid can completely come to rest during the uncontrolled turbulence occuring in the available volume. During the atomization, these regions low in interchange are only filled with fresh aerosol following a large time-lag and are only emptied with difficulty again during inhalation. About 3 to 5 breaths are required for complete evacuation. On account of the long sojourn time in these regions, the droplets can settle on the walls of the stilling chamber. Therefore, the stilling and the homogenization of the vaporized liquid in such systems is insufficient. A further disadvantage is the large volume required which is difficult to handle for the patient in particular, in transportable inhalation devices.

An inhalation vessel of plastic is known from the German utility model G 89 08 273 which has a specialized shape in order to reduce the dimensions. The oblong main body of the stilling chamber, which at its one end, has a connecting piece for the supply of the vaporized liquid and at its other end, a withdrawal piece, consists as a whole of an amphora-like shape in which a short transition region connects with the connecting piece to enable the elliptical section of the connecting part to change over into a circular shape and from there to make up the shape of the main body in the form of a continuously increasing circular cross-section until it approaches the size of the withdrawal part again through a constantly decreasing circular cross-section after reaching a largest diameter. Thus, the cross-section of this known stilling chamber increases continously in the direction of the aerosol stream beginning with the diameter of the connecting part, and then decreases to the cross-section of the withdrawal part shortly before reaching this. However, this known inhalation vessel is actually also a very large structure in which a homogenization and deceleration of the vaporized liquid together with the simultaneous provision of a sufficient volume is achieved only with the limitation regarding its total size and thus, the ease of handling in favor of the functional purpose.

An inhalation vessel is also known which has a cylindrical atomizing space at the one front side of which a spray diffuser is centrally provided. The opposing front end of the cylindrical space has a central T-piece as a connecting element for the withdrawal part via which the inhalation ensues. In order to influence the air stream in the cylindrical space with regard to a homogenization and stilling of the vaporized liquid, a calotte, almost completely closing the cylindrical space towards the top, is provided which consists of an opening provided in its central region for the T-piece. In the peripheral region of the calotte, air flowing in from the top is guided along the outer walls of the cylindrical hollow body so that a mixing-through of the air with the vaporized liquid entering from the bottom is achieved.

SUMMARY OF THE INVENTION

Accordingly, it is an object of the invention to provide an atomizer, in particular for use in devices for inhalation therapy, which for small dimensions effects a stilling as well as a homogenization of the supplied vaporized liquid and makes available a volume sufficient for the inhalation act.

This object is solved by an atomizer with a cylindrical atomizing space, an opening for the supply of vaporized liquid and an opening for the withdrawal of vaporized liquid which is structured in accordance with the invention such that at least one of the openings is arranged in such a manner that a spiral vortex extending about the longitudinal axis of the atomizing space is formed within the atomizing space.

Further embodiments of the invention are set forth hereinafter.

BRIEF DESCRIPTION OF THE DRAWINGS

The invention is described in more detail in the following on the basis of exemplified embodiments and with reference to the drawings, in which:

FIG. 1 shows the arrangement of a first exemplified embodiment of an atomizer according to the invention; and FIG. 2 shows the arrangement of a second exemplified embodiment of an atomizer according to the invention.

DESCRIPTION OF PREFERRED EMBODIMENTS

Figure 1:
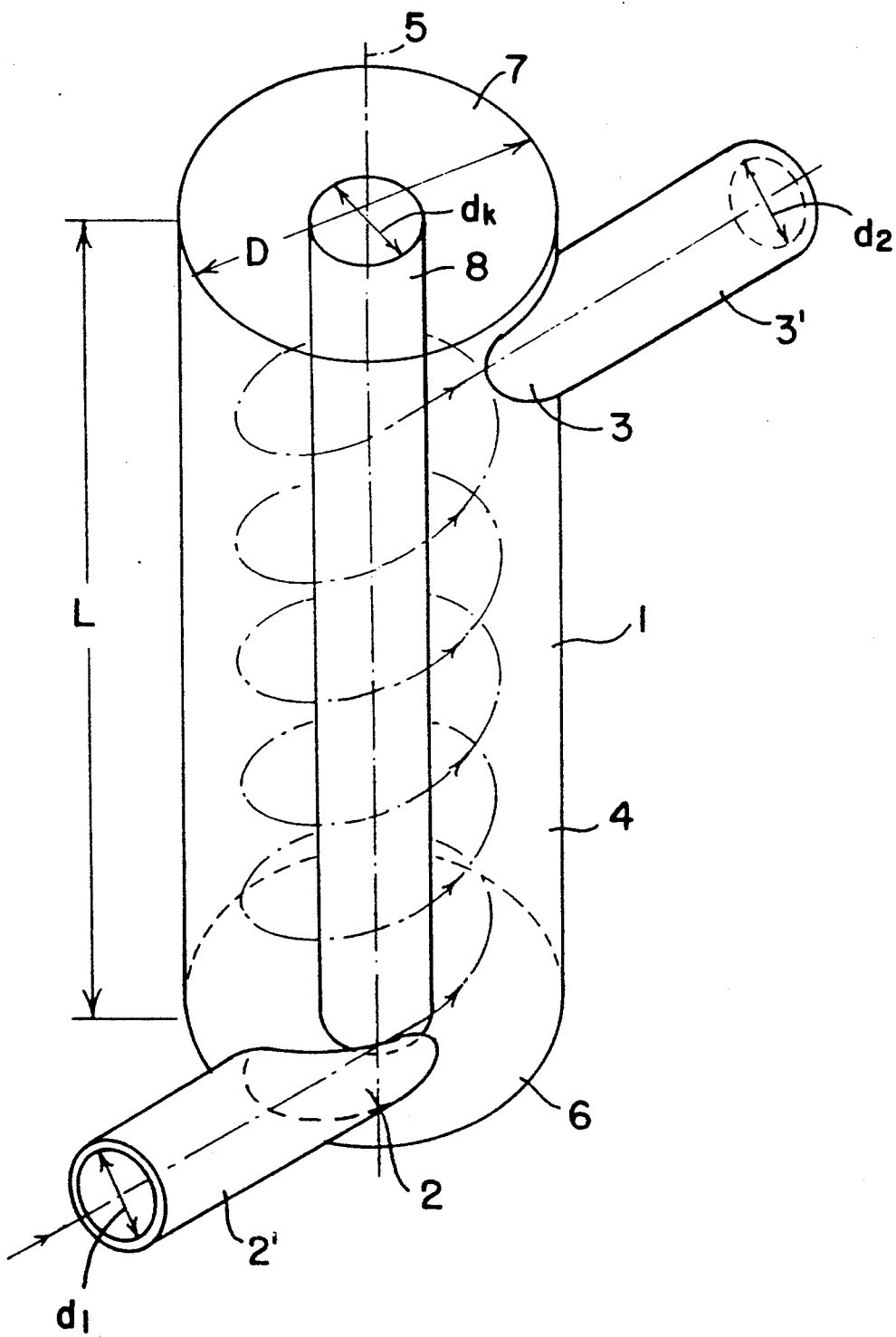

The atomizer according to the invention depicted in FIG. 1 has a cylindrical atomizing space 1 which consists of an opening 2 for the supply of a vaporized liquid vapor and an opening 3 for the withdrawal of the vaporized liquid. Both openings 2 and 3 are arranged in the wall of the cylindrically shaped atomizing space 1 in a manner according to the invention such that the connecting pieces 2' and 3', respectively provided at the opening 2 and 3, enter tangentially into the wall 4 and hence, have their axes tangent to a circle having its center at the longitudinal axis 5. For this reason, the openings 2 and 3 therefore lie laterally displaced with respect to the longitudinal axis 5 so that a spiral vortex is formed in supplying the vaporized liquid through the opening 2 and withdrawing it through the opening 3, the spiral vortex leading to the filling and flushing of the atomizing space 1. With this, an even distribution and a deceleration of the liquid droplets and thus, a homogenization of the vaporized liquid is achieved on account of the spiral vortex.

In this exemplified embodiment, the formation of the spiral vortex is ensured on account of the arrangement of both openings 2 and 3 as the supply and the withdrawal of the active substance aerosol from the cylindrical atomizing space ensue tangentially. The opening 3, laterally displaced with respect to the longitudinal axis 5, is arranged so that the spiral vortex which is formed practically enters into the opening 3 after the introduction of the vaporized liquid. However, the liquid droplets have been decelerated along the path through the atomizing space, which is extended on account of the spiral vortex, to such an extent that an undesirably strong aerosol stream at the opening 3 is avoided.

The position of the openings 2 and 3, in the direct vicinity of the ends 6 and 7 of the cylindrical atomizing space 1, ensures an optimal utilization of the available volume of the atomizing space 1 and a path which is as long as possible with the same sojourn time for the liquid droplets.

When an aerosol of a substance is supplied via the connection piece 2' and the opening 2 into an emptied atomizing space 1, the atomizing space 1 then fills up through the formation of a spiral vortex having a small pitch so that the liquid droplets which have entered fill up the atomizing space beginning from the region of the opening 2. On account of the small pitch, a very long path results for the liquid droplets which corresponds to a multiple of the length of the cylindrically shaped atomizing space 1. In the filling step, a homogeneous vaporized liquid of suspended liquid droplets forms within the atomizing space 1 which is sucked off completely in the breathing-in phase of the inhalation act through the opening 3 and via the connecting piece 3' with a single breath. With this, however, an active substance aerosol can still be continuously supplied through the opening 2.

During the filling step, only the air volume flow required for the atomization flows through the atomizing space 1 so that an aerosol with a high droplet concentration ensues. During breathing, the volume flow which is carried through increases corresponding to the breath drawn by the patient so that the following aerosol stream has a considerably lower concentration. The spiral vortex then resulting has a greater pitch as the flow of the liquid droplets in the atomizing space 1 is accelerated by the suction step via the opening 3. However, a sufficient deceleration of the liquid droplets is achieved as the length of passage is still considerably greater than the actual length of the cylindrical atomizing space 1 on account of the spiral vortex. The homogenization of the vaporized liquid is also ensured in the formation of the spiral vortex which arises during the suction step.

In the exhaling phase, a flow of the inhaled air back into the atomizing space 1 is prevented in a known manner, such as by means of a non-return valve. Thus, an interference in the formation of the spiral vortex is prevented so that during the exhaling phase of the inhalation act, the filling of the atomizing space 1 by means of the vaporized liquid supplied through the opening 2 newly ensues with the formation of a spiral vortex having a small pitch with a high droplet concentration.

The volume of the atomizing space 1 must be determined such that on the one hand, a large part of the breathing volume of the patient is accounted for and, on the other hand, the entire atomizing space can be filled again with highly concentrated aerosol during the exhaling phase. With this, the aerosol arising during inhaling is forced out of the atomizing space with a low particle concentration during inhaling. The loss of substance resulting from this is, however, low in comparison to common, continuously operated atomizing systems.

Atomizers which have a volume of 200 to 350 ml (adult) or 100 to 200 ml (child) were found to be particularly suitable for practical use under consideration of the previously revealed aspects. The dimensions L and D indicated in FIG. 1 are advantageously to be selected with a ratio L/D of about 2 to 3. Preferably, the volume amounts to 300 ml (adult) or 150 ml (child) and the ratio L/D about 2.5.

The formation of the spiral vortex can be further supported by the provision of an equally cylindrical central part 8 in the middle of the atomizing space 1 which extends in the longitudinal direction and the longitudinal axis of which coincides with the longitudinal axis 5 of the atomizing space 1. With this, the central part 8 can have a constant cross-section as shown in FIG. 1 or a cross-section which changes and influences the velocity of the liquid droplets. The function of the central part 8 supporting the formation of the spiral vortex is essential in this case, and can lead to a multiplicity of structural possibilities. An important structural criterion is, for example, a fast and complete evacuation of the concentrated aerosol in the inhaling phase with the aim of substantially maintaining constant the sojourn period of the inflowing liquid droplets and safeguarding an optimal utilization of the available storage volume, of the atomizing space 1 for the acceptance of the vaporized liquid.

The diameter $d_k$ of the central part is advantageously selected such that the ratio $D/d_k$ amounts to approximately 2.5 to 3.5, preferably, 3.0. The diameters $d_1$ and $d_2$ of the respective connecting pieces 2' and 3' advantageously fulfill the equation $d_1/d_k = 0.5$ to 1.5 and $d_2/d_k = 0.5$ to 1.5, and preferably, the equation $d_1 = d_2 = d_k$.

Figure 2:
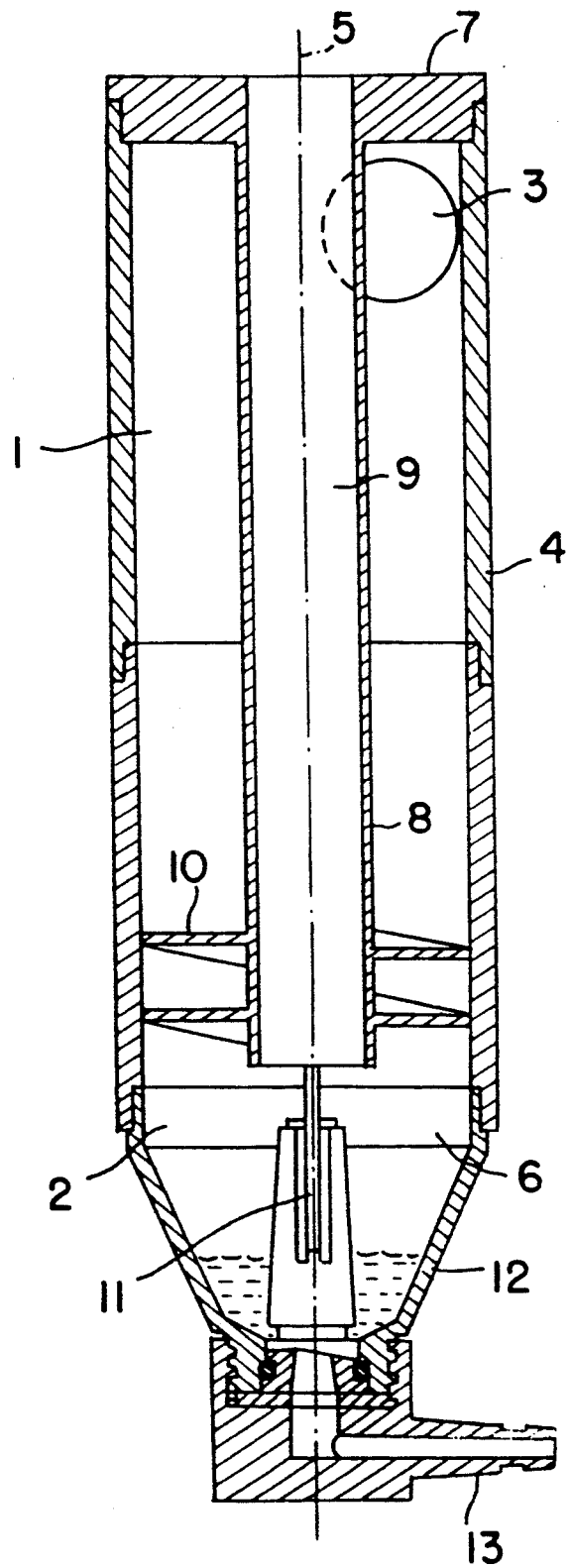

In FIG. 2, a second exemplified embodiment of the inventive atomizer is depicted in connection with a diffuser. The essentially cylindrically-shaped atomizing space 1 has a wall 4 in which an opening 3 for the withdrawal of the vaporized liquid is arranged laterally displaced with respect to the longitudinal axis 5 so that a spiral vortex is formed about the longitudinal axis 5 during the withdrawal of the liquid vapor. The opening 3 is provided in the wall 4 in the vicinity of one end 7 of the atomizing space 1. A connecting piece is formed at the opening 3.

The opening 2 for supplying the vaporized liquid is arranged at the end 6 of the atomizing space 1 in this exemplified embodiment. The opening 2 comprises the entire cross-sectional area of the cylindrical atomizing space. For supporting the formation of the spiral vortex in the atomizing space 1, a central part 8 in the form of a cylindrical hollow body is provided, the longitudinal axis of which coincides with the longitudinal axis 5 of the atomizing space. The central part penetrates the side wall closing off the end 7 of the atomizing space 1 so that an air supply channel 9 is formed which extends through the atomizing space 1 from the end 7 to its opposing end and ends in the region of the opening 2 for the supply of the vaporized liquid.

Guiding surfaces 10 are arranged at the end of the central part 8 on its outer wall and project into the atomizing space 1, the guiding surfaces extending helically in the manner of the ensuing spiral vortex about the central part 8. It can be seen in FIG. 2 that the guiding surfaces close the atomizing space 1 towards the opening 2 as seen in the longitudinal direction as these guiding surfaces extend from the outer surface of the central part 8 to the inner wall of the surface 4 of the atomizing space 1.

A spray diffuser 11 diffuses the liquid present in the conical end section 12 when pressurized air is supplied via the connecting pipe 13.

During the inhalation act, an air stream is generated during the breathing-in phase which extends through the air supply channel 9 in the central part 8 past the spray diffuser 11 and the surfaces of the guiding element 10 up to the opening 3 for the withdrawal of the vaporized liquid. The laterally displaced arrangement of the opening 3 leads to the formation of the spiral vortex in the atomizing space 1 in the breathing-in phase of the inhalation act. This act is supported by the central part 8 which simultaneously serves as a feed element for external air, and by the helical guiding element 10 at the end of the central part 8 which is located in the direct vicinity of the opening 2 for the supply of the vaporized liquid.

On account of the fact that the helical guiding element 10 closes the atomizing space 1, the further advantage ensues whereby liquid droplets which are too large are already separated in the lower region of the arrangement and the liquid collects again together with the substance in the conical end section. From here, it again approaches the spray diffuser 11 and goes back into the atomizing circulation.

The sizes or dimensions already indicated above are also valid for the second exemplified embodiment.

We claim:

1. An inhalation therapy atomizer for supplying a vaporized liquid to a patient, said atomizer comprising:

a tubular housing having a wall, a first end and a second end spaced from said first end and a longitudinal axis extending from said first end to said second end, said housing having an interior wall surface of substantially constant radius around said axis;

a central member with a cylindrical exterior surface disposed within said housing with the axis of said cylindrical surface co-axial with said axis of said housing, said cylindrical exterior surface having a radius less than said radius of said interior wall surface, said cylindrical exterior surface and said interior wall surface defining an atomizing space therebetween;

said tubular housing having a first opening at said first end for supplying vaporized liquid to said atomizing space and a second opening at said second end for withdrawing vaporized liquid from said atomizing space, at least one of said first opening and said second opening extending through said wall; and vapor directing means connected to said one of said first opening and said second opening for directing said vapor along a spiral path extending from said one of said first opening and said second opening to the other of said first opening and said second opening, said path being spaced from said axis and extending around said axis.

2. An atomizer as set forth in claim 1 wherein said one of said first opening and said second opening is said first opening.

3. An atomizer as set forth in claim 2 wherein said second opening also extends through said wall and further vapor directing means is connected to said second opening for directing said vapor along said path.

4. An atomizer as set forth in claim 1 wherein said one of said first opening and said second opening is said second opening.

5. An atomizer as set forth in claim 4 wherein said first opening is transverse to said longitudinal axis of said housing.

6. An atomizer as set forth in claim 5 wherein said first opening has a radius substantially equal to said radius of said cylindrical exterior surface.

7. An atomizer as set forth in claim 4 wherein there is helical guiding means adjacent said first opening and in said atomizing space for augmenting the flow of said vapor along said spiral path.

8. An atomizer as set forth in claim 7 wherein said HELICAL GUIDING means comprises means with a helical surface extending helically around said central member and from said cylindrical exterior surface to said interior wall surface.

9. An atomizer as set forth in claim 8 wherein said central member has a tubular bore which extends from one of said first end and said second end to said second opening for supplying air to said second opening.

10. An atomizer as set forth in claim 1 wherein the ratio of said radius of said interior wall surface to said radius of said interior wall surface is in the range from about 2.5 to about 3.5.

11. An atomizer as set forth in claim 1 wherein the volume of said atomizing space is in the rang from about 100 to about 350 milliliters.

12. An atomizer as set forth in claim 1 wherein the ratio of the length of said atomizing space in the direction of said axis of said housing to the diameter of said interior wall surface is in the range from about two to about three.

13. An atomizer as set forth in claim 1 or 3 wherein said vapor directing means comprises a tubular connecting means having an axis extending tangentially to a circle having its center at said axis of said tubular housing and hence, laterally of said axis of said housing.

14. An atomizer as set forth in claim 1 wherein said vapor directing means comprises a tubular connecting means having an axis extending other than at said axis of said tubular housing and said tubular connecting means has an internal radius which is in the range from about 0.5 to about 1.5 times said radius of said cylindrical exterior surface.

* * * * *